US012565681B2

(12) United States Patent (10) Patent No.: US 12,565,681 B2

Hung et al. (45) Date of Patent: Mar. 3, 2026

(54) METHOD AND A KIT FOR PREDICTING THE SUSCEPTIBILITY TO STIMULATOR OF INTERFERON GENES (STING) AGONISTS IN A CANCER PATIENT

(71) Applicant: China Medical University, Taichung City (TW)

(72) Inventors: Mien-Chie Hung, Taichung City (TW); Jung-Mao Hsu, Taichung City (TW)

(73) Assignee: China Medical University, Taichung City (TW)

( * ) Notice: Subject to any disclaimer, the term of this patent is extended or adjusted under 35 U.S.C. 154(b) by 807 days.

(21) Appl. No.: 17/744,669

(22) Filed: May 14, 2022

(65) Prior Publication Data

US 2022/0364181 A1 Nov. 17, 2022

Related U.S. Application Data

(60) Provisional application No. 63/189,228, filed on May 17, 2021.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57484* (2013.01); *C12Q 2600/106* (2013.01); *C12Q 2600/158* (2013.01)

(58) Field of Classification Search
CPC ............ C12Q 1/6886; C12Q 2600/106; C12Q 2600/158; C12Q 2600/118; G01N 33/57484
See application file for complete search history.

(56) References Cited

FOREIGN PATENT DOCUMENTS

WO WO-2015077354 A1 * 5/2015 ........... A61K 31/352

OTHER PUBLICATIONS

Hellerbrand et al. Promoter-hypermethlation is causing functional relevant downregulation of methylthioadenosine phosphorylase (MTAP) expressin in hepatocellular carcinoma. Carcinogenesis 27(1): 64-72, 2006.*

Liu et al. STING, a promising target for small molecular immune modulator: A review. European Journal of Medicinal Chemistry 211: 1-31, available online Dec. 18, 2020.*

Conlon J, Burdette DL, Sharma S, Bhat N, Thompson M, Jiang Z, Rathinam VA, Monks B, Jin T, Xiao TS, Vogel SN, Vance RE, Fitzgerald KA. Mouse, but not human STING, binds and signals in response to the vascular disrupting agent 5,6-dimethylxanthenone-4-acetic acid. J Immunol. May 15, 2013; 190(10):5216-25.

* cited by examiner

*Primary Examiner* — Alana Harris Dent

(74) *Attorney, Agent, or Firm* — Hannah Tien

(57) ABSTRACT

A method for predicting susceptibility to stimulator of interferon genes (STING) agonists of a cancer patient is provided, comprising (1) obtaining at least one sample from the cancer patient; (2) detecting an expression level of S-methyl-5'-thioadenosine phosphorylase (MTAP) in the at least one sample by using at least one specific probe; and (3) if MTAP is expressed in the at least one sample, then predicting that the cancer patient has high-susceptibility to STING agonists and providing STING agonists to treat the cancer patient; otherwise providing non-STING agonists for treatment.

5 Claims, 4 Drawing Sheets

METHOD AND A KIT FOR PREDICTING THE SUSCEPTIBILITY TO STIMULATOR OF INTERFERON GENES (STING) AGONISTS IN A CANCER PATIENT

FIELD OF THE INVENTION

The present invention relates to a method for predicting susceptibility to stimulator of interferon genes (STING) agonists of a cancer patient, particularly to a method for predicting susceptibility to STING agonists of a cancer patient by detecting an expression level of S-methyl-5'-thioadenosine phosphorylase (MTAP); and the present invention further relates to a kit for predicting susceptibility to STING agonists of a cancer patient, particularly to a kit for predicting susceptibility to STING agonists of a cancer patient by detecting an expression level of MTAP.

BACKGROUND OF THE INVENTION

Cancer has always been one of the health issues that mankind desires to overcome the most. The research on cancer treatment has always been the goal of improvement pursued by mankind. As a result of long-term and dedicated research and development of cancer treatment, current cancer treatment methods include radiation therapy, surgery, chemotherapy and targeted therapy.

Recently, new researches indicate that stimulator of interferon genes (STING) can facilitate the production of type I interferon (IFN) in the body, and type I interferon is essential to the generation of anti-tumor CD8+ T cells, therefore the development of stimulator of interferon genes agonist (STING agonist) is the key development project of many pharmaceutical companies.

However, it is still unclear for which types of cancer suffered by patients the STING agonists are suitable, and the urgent problem to be solved is to find cancer patients who are suitable for STING agonists so as to provide the most accurate medical treatment.

SUMMARY OF THE INVENTION

The present invention is a method for predicting susceptibility to stimulator of interferon genes (STING) agonists of a cancer patient, comprising
- (1) obtaining at least one sample from the cancer patient,
- (2) detecting an expression level of S-methyl-5'-thioadenosine phosphorylase (MTAP) in the at least one sample by using at least one specific probe; and
- (3) if the at least one sample from the cancer patient shows high expression level of MTAP, then predicting that the cancer patient has high-susceptibility to STING agonists and providing STING agonists to treat the cancer patient; otherwise providing non-STING agonists for treatment.

BRIEF DESCRIPTION OF THE DRAWINGS

FIG. 1A shows the result of the western blot, confirming that the MTAP gene in the MTAP(–) Group is indeed deleted; FIG. 1B and FIG. 1D show the results of Enzyme-linked immunosorbent assay (ELISA), showing that STING agonists indeed have the effect of stimulating the expression of interferon β (IFN β), and in the MTAP(+) cells, STING agonists effectively stimulate the expression of IFN β, but the effect of STING agonists on the expression of interferon β (IFN β) in the MTAP(–) cells is significantly lower; FIG. 1C and FIG. 1E show that the gene expression level of IFN β gene (IFNb1) and interferon-stimulated genes MX1 and ISG15 of the MTAP(–) STING Group is significantly lower than these genes in the MTAP(+) STING Group.

FIG. 2A shows the result of the western blot, confirming that the MTAP gene in the MTAP(–) Group is indeed deleted; FIGS. 2B and 2D are the results of the enzyme-linked immunosorbent assay (ELISA), showing that STING agonists indeed have the effect of stimulating the expression of interferon β (IFN β), and in the MTAP(+) cells, STING agonists effectively stimulate the expression of IFN β, but the effect of STING agonists on the expression of interferon β (IFN β) in the MTAP(–) cells is significantly lower; FIG. 2C and FIG. 2E show that the gene expression levels of IFN β gene (IFNb1) and interferon-stimulated genes MX1 and ISG15 in the MTAP(–) STING Group are significantly lower than these genes in the MTAP(+) STING Group.

DETAILED DESCRIPTION OF THE INVENTION

Figure 1A:
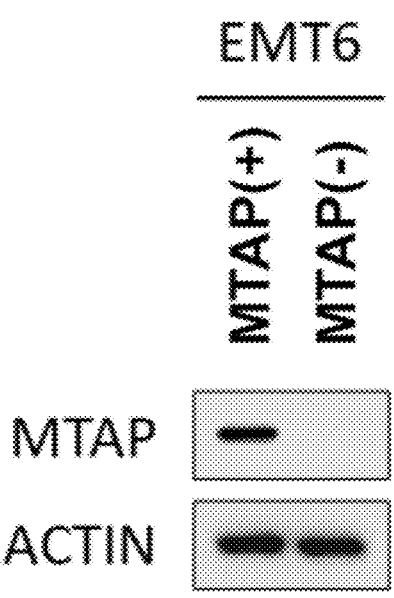
FIGS. 1A-1E are the results of in vitro assays of susceptibility to STING agonists of EMT6 cell lines.
Figure 1B:
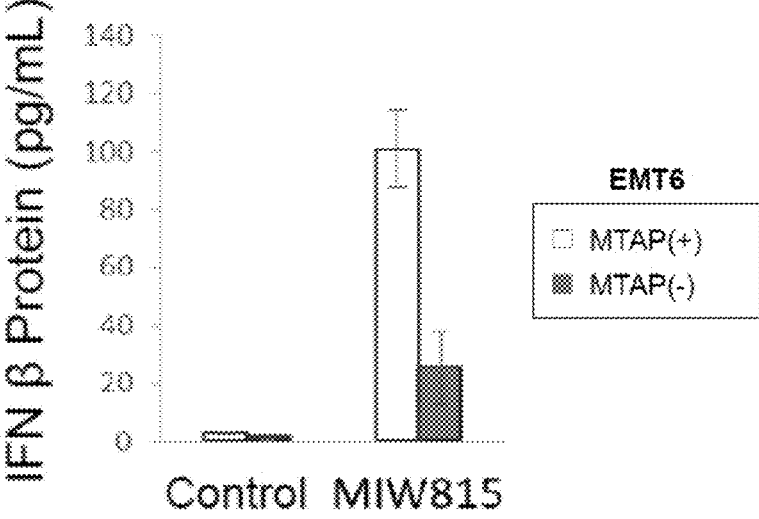
Figure 1C:
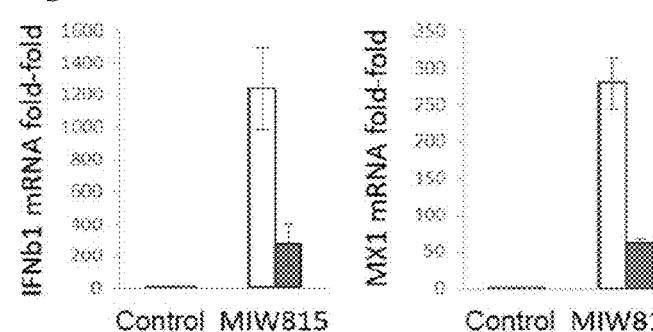
Figure 1D:
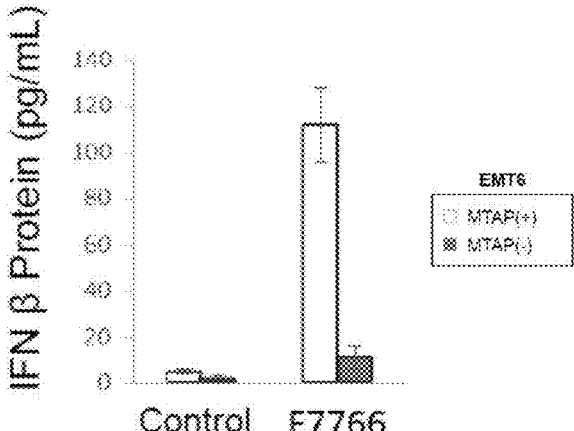
Figure 1E:
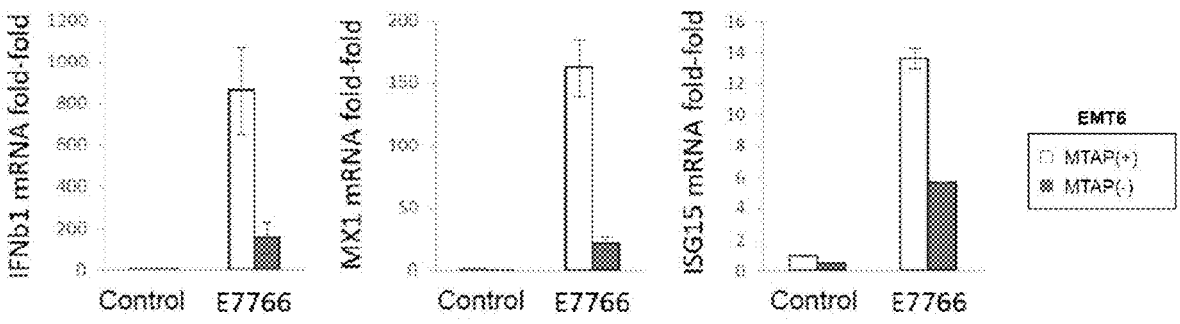

The present invention is a method for predicting susceptibility to stimulator of interferon genes (STING) agonists of a cancer patient, comprising
- (1) obtaining at least one sample from the cancer patient,
- (2) detecting an expression level of S-methyl-5'-thioadenosine phosphorylase (MTAP) in the at least one sample by using at least one specific probe; and
- (3) if MTAP is expressed in the at least one sample, then predicting that the cancer patient has high-susceptibility to STING agonists and providing STING agonists to treat the cancer patient; otherwise providing non-STING agonists for treatment.

In the present invention, wherein the expression level of the S-methyl-5'-thioadenosine phosphorylase (MTAP) is the expression level of genes, the expression level of mRNAs, or the expression level of proteins.

In the present invention, wherein the expression level of S-methyl-5'-thioadenosine phosphorylase (MTAP) in the at least one sample is detected by a detecting method, wherein the detecting method includes, but not limited to, fluorescent in situ hybridization, (FISH), genome sequencing, immunohistochemistry (IHC), DNA microarray, or western blot.

In the present invention, wherein the at least one sample comprises blood, cancer tissues, urine, lacrimal fluid or saliva.

The present invention further provides a kit for predicting susceptibility to stimulator of interferon genes (STING) agonists of a cancer patient, comprising a S-methyl-5'-thioadenosine phosphorylase (MTAP) specific probe for detecting an expression level of the S-methyl-5'-thioadenosine phosphorylase (MTAP) in at least one sample obtained from the cancer patient.

In the present invention, wherein the specific probe is selected from a specific primer pair or a specific antibody.

DESCRIPTION OF EMBODIMENTS

One skilled in the art readily appreciates that the present invention is well adapted to carry out the objects and obtain the ends and advantages mentioned, as well as those inherent therein. The compositions, processes and methods for producing them, and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

Cell Assays

Two cancer cell lines, the mouse mammary carcinoma cell line EMT6 and the mouse colon adenocarcinoma cell line MC38, were used in the present invention as the models of cell assays. Both cell lines were cultured in accordance with the culture method suggested in the instructions.

These two cancer cell lines were divided into two groups, one group was treated with cell culture medium, and named as MTAP(+); the other group was treated with siRNA of the S-methyl-5'-thioadenosine phosphorylase (MTAP) for gene knock-out, and named as MTAP(−).

A portion of the cells were removed to confirm by western blot whether or not MTAP was indeed deleted.

In Vitro Assay for Susceptibility to STING Agonists

In the present invention, two cancer cell lines (EMT6 cell line and MC38 cell line) of MTAP(+) and MTAP(−) were stimulated with STING agonists, and then the expression level of Type I Interferon was measured to determine the activity of the STING agonists.

The STING agonists used in the present invention included MIW815 and E7766, and two cells were divided into six groups, respectively, the MTAP(+) Control Group, the MTAP(−) Control Group, MTAP(+) MIW815 Group, MTAP(+) E7766 Group, MTAP(−) MIW815 Group and MTAP(−) E7766 Group.

In this assay, after culturing the EMT6 cell line and the MC38 cell line for 12 hours, the medium of the cells in the MTAP(+) STING Group and the MTAP(−) STING Group were replaced with a medium containing 100 μg/mL of STING agonists, and then subjected to stimulation for 24 hours.

The cells were harvested, and a portion of the cells was used for enzyme-linked immunosorbent assay (ELISA) to detect the expression level of interferon β (IFN β); the other portion was used for extraction of mRNA with TRizol, and then real-time quantitative reverse transcription polymerase chain reaction (RT-qPCR) was used to amplify its DNA fragments for detecting the gene expression levels of the interferon beta gene (IFNb1) and interferon-stimulated genes MX1 and ISG15.

Animal Experiments

In the present invention, the EMT6 cell lines with expressed MTAP (MTAP(+) Group) and the EMT6 cell lines with no expressed MTAP (MTAP(−) Group) were inoculated into mice for in vivo assays of the activity of STING agonists.

In this experiment, MIW815 was selected as the STING agonist, and the mice were divided into 4 groups, 5 mice in each group, namely the MTAP(+) Control Group, the MTAP(−) Control Group, the MTAP(+) MIW815 Group and the MTAP(−) MIW815 Group.

Drugs were administered after the cancer cells grew to be more than 100 mm³. Phosphate buffered saline solution (PBS) was given to the MTAP(+) Control Group and the MTAP(−) Control Group; and 50 μg of STING agonist MIW815 was given to the MTAP(+) MIW815 Group and the MTAP(−) MIW815 Group at Day 9, 12 and 16. The tumor size of each group of the mice was observed at Day 4, 7, 8, 12, 16 and 19, and statistical analysis was conducted.

Results

Figure 2A:
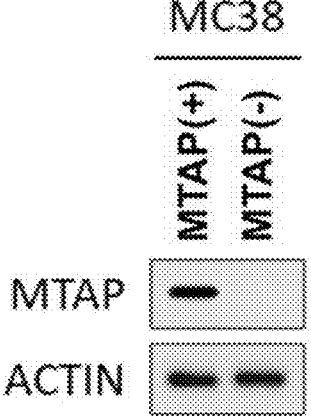
FIGS. 2A-2D are the results of in vitro assays of susceptibility to the STING agonists of MC38 cell line.
Figure 2B:
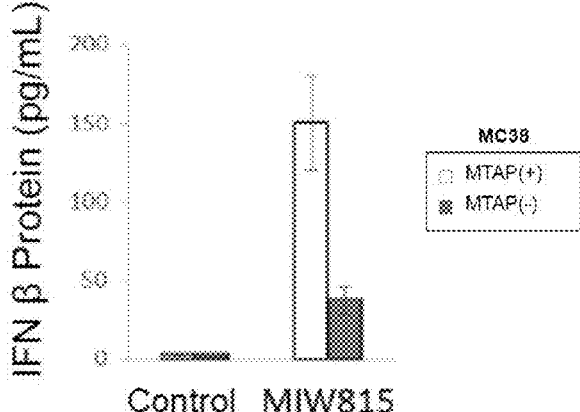
Figure 2C:
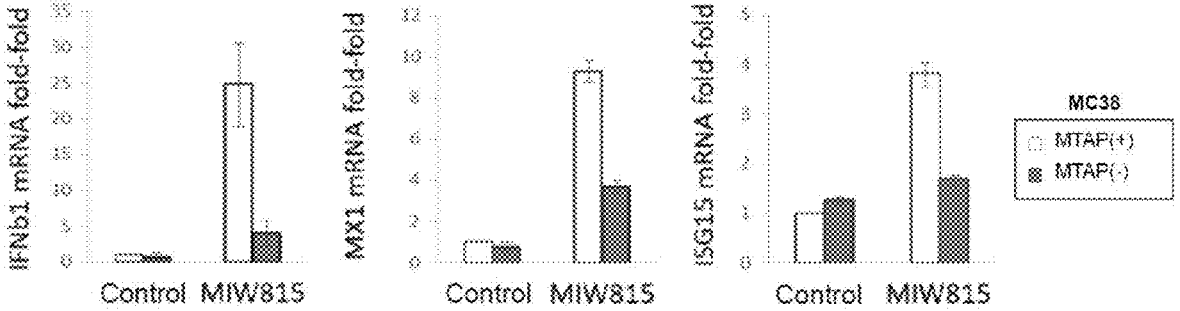
Figure 2D:
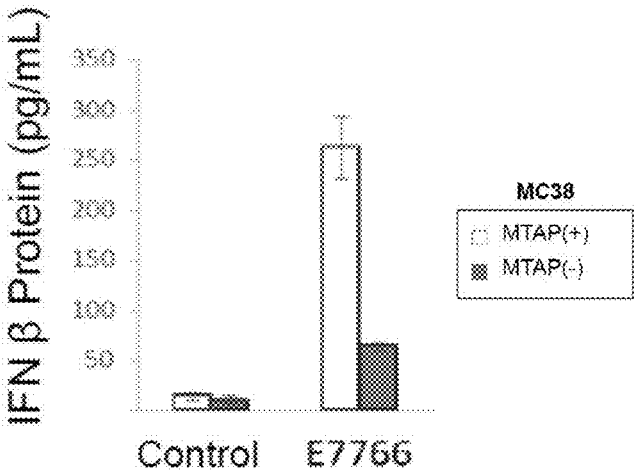
Figure 2E:
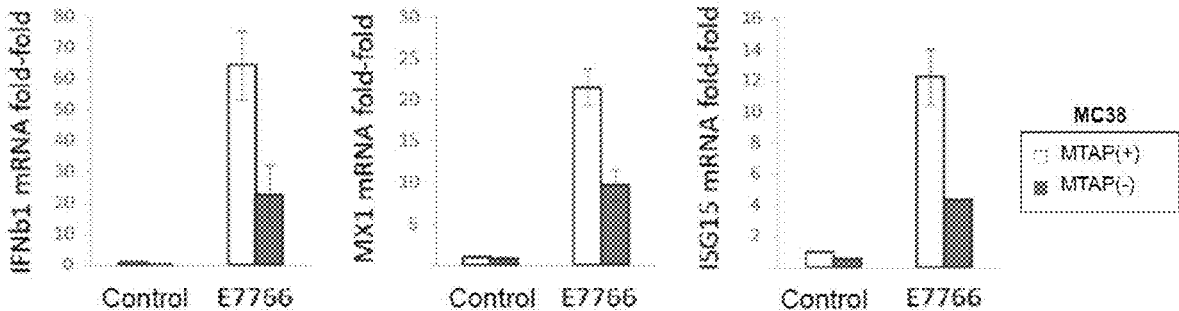

As shown in FIG. 1A and FIG. 2A, after confirming by western blot that the MTAP gene was successfully knocked out in the EMT6 cell line and the MC38 cell line, in vitro assays of the susceptibility to STING agonists were performed.

The results of the in vitro assays showed that after the EMT6 cell line and the MC38 cell line were stimulated with two STING agonists, MIW815 and E7766, the results of the expression of Interferon β (IFN β) were in fact produced (FIG. 1B, FIG. 1D, FIG. 2B and FIG. 2D), and in the MTAP(+) cells, the STING agonists effectively stimulated the expression of IFN β, but the effect of stimulating Interferon β (IFN β) by the STING agonists in the MTAP(−) cells was significantly lower.

As shown in FIG. 1C, FIG. 1E, FIG. 2C and FIG. 2E, the results of RT-qPCR also indicate that the gene expression levels of the IFN β gene (IFNb1) and the genes of the interferon-stimulated genes MX1 and ISG15 in the MTAP (−) STING Group were significantly lower than those of these genes in the MTAP(+) STING Group.

This result shows that when the cancer cells expressed MTAP, the susceptibility to STING agonists was high; but when the cancer cells did not express MTAP, the susceptibility to STING agonists was significantly reduced.

Figure 3:
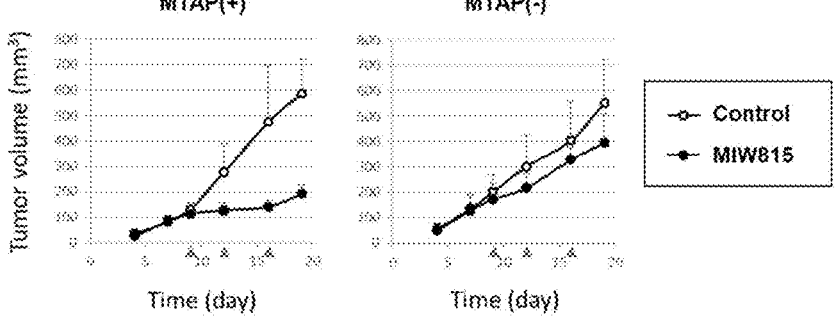
FIG. 3 shows the anti-tumor proliferation results in animal experiments.

The results of animal experiments discovered that in the MTAP(+) Group, the tumor size of the MTAP(+) MIW815 Group was significantly smaller than the MTAP(+) Control Group; in the MTAP(−) Group, the results show that the tumor size of the MTAP(−) MIW815 Group was not statistically different from that of the MTAP(−) Control Group (FIG. 3).

Based on the above results, it is known that the homozygous deletion of MTAP gene in the cancer cells can inhibit the activity of STING agonists. Therefore, the present invention considers that deletion of MTAP detected in the cancer cells can be used for screening cancer patients who are suitable for being treated with STING agonists. When it is determined that the cancer patient is highly susceptible to STING agonists, STING agonists are considered to be suitable for treatment, so that medical orders of treating cancer patients with STING agonists can be given, otherwise other treatment modalities should be used.

What is claimed is:

1. A method for treating a cancer patient with high-susceptibility to stimulator of interferon genes (STING) agonists, comprising:
    (1) obtaining at least one sample from a cancer patient;
    (2) detecting an expression level of S-methyl-5'-thioadenosine phosphorylase (MTAP) in the at least one sample by using at least one specific probe;
    (3) predicting the cancer patient is high-susceptible to STING agonists when MTAP is expressed in the at least one sample; and
    (4) treating the cancer patient with high-susceptibility to STING agonists with STING agonists, wherein the STING agonists are IFNb1 gene stimulator agonists.

2. The method of claim 1, wherein the specific probe is selected from a specific primer pair or a specific antibody.

3. The method of claim 1, wherein the expression level of the S-methyl-5'-thioadenosine phosphorylase (MTAP) is the expression level of genes, the expression level of mRNAs, or the expression level of proteins.

4. The method of claim 1, wherein the expression level of S-methyl-5'-thioadenosine phosphorylase (MTAP) in the at least one sample is detected by a detecting method, wherein the detecting method includes, but not limited to, fluorescent in situ hybridization, (FISH), genome sequencing, immuno-histochemistry (IHC), DNA microarray, or western blot.

5. The method of claim 1, wherein the at least one sample comprises blood, cancer tissues, urine, lacrimal fluid or saliva.

\* \* \* \* \*